US007829288B2

(12) United States Patent
Kornblith et al.

(10) Patent No.: US 7,829,288 B2
(45) Date of Patent: *Nov. 9, 2010

(54) METHODS FOR ASSESSING EFFICACY OF CHEMOTHERAPEUTIC AGENTS

(75) Inventors: Paul L. Kornblith, Pittsburgh, PA (US); Sean McDonald, Pittsburgh, PA (US)

(73) Assignee: Precision Therapeutics, Inc., Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/510,671

(22) Filed: Jul. 28, 2009

(65) Prior Publication Data

US 2009/0286255 A1 Nov. 19, 2009

Related U.S. Application Data

(63) Continuation of application No. 11/713,662, filed on Mar. 5, 2007, now Pat. No. 7,575,868, which is a continuation of application No. 10/336,659, filed on Jan. 2, 2003, now abandoned.

(60) Provisional application No. 60/417,439, filed on Oct. 10, 2002.

(51) Int. Cl.
*C12Q 1/68* (2006.01)
*C07H 21/02* (2006.01)
*C07H 21/04* (2006.01)

(52) U.S. Cl. .......................... 435/6; 536/23.1; 536/24.3
(58) Field of Classification Search .................... 435/6; 536/23.1, 24.3
See application file for complete search history.

(56) References Cited

U.S. PATENT DOCUMENTS

| | | | | |
|---|---|---|---|---|
| 4,423,145 | A | 12/1983 | Stampfer et al. | 435/32 |
| 4,559,299 | A | 12/1985 | Rotman | |
| 4,668,618 | A | 5/1987 | Thornthwaite | |
| 4,816,395 | A | 3/1989 | Hancock et al. | |
| 4,937,187 | A | 6/1990 | Rotman | 435/30 |
| 4,996,145 | A | 2/1991 | Weisenthal | 435/7.23 |
| 5,242,806 | A | 9/1993 | Yen-Maguire et al. | 435/32 |
| 5,270,172 | A | 12/1993 | Morgan | 435/29 |
| 5,403,574 | A | 4/1995 | Piwnica-Worms | |
| 5,443,950 | A | 8/1995 | Naughton et al. | |
| 5,607,918 | A | 3/1997 | Eriksson et al. | |
| 5,705,270 | A | 1/1998 | Soon-Shiong et al. | |
| 5,728,541 | A * | 3/1998 | Kornblith | 435/29 |
| 5,789,158 | A | 8/1998 | Knowles et al. | |
| 5,874,218 | A | 2/1999 | Drolet et al. | |
| 5,888,765 | A | 3/1999 | Patterson et al. | |
| 5,942,385 | A | 8/1999 | Hirth | 435/4 |
| 5,972,639 | A | 10/1999 | Parandoosh | 435/29 |
| 6,008,007 | A | 12/1999 | Fruehauf et al. | 435/29 |
| 6,020,473 | A | 2/2000 | Keyt et al. | |
| 6,111,092 | A | 8/2000 | Williamson | |
| 6,261,795 | B1 | 7/2001 | Fruehauf et al. | 435/29 |
| 6,303,324 | B1 | 10/2001 | Fruehauf | 435/7.23 |
| 6,335,170 | B1 | 1/2002 | Orntoft | 435/6 |
| 6,416,967 | B2 | 7/2002 | Kornblith | 435/29 |
| 6,511,806 | B1 | 1/2003 | Fruehauf et al. | 435/6 |
| 6,664,062 | B1 | 12/2003 | Stanton, Jr. | |
| 6,900,027 | B1 * | 5/2005 | Kornblith | 435/29 |
| 6,933,129 | B1 * | 8/2005 | Kornblith | 435/29 |
| 7,501,260 | B2 * | 3/2009 | Kornblith | 435/29 |
| 7,575,868 | B2 * | 8/2009 | Kornblith et al. | 435/6 |
| 2002/0168679 | A1 | 11/2002 | Naus et al. | |
| 2002/0192638 | A1 | 12/2002 | Kornblith | |
| 2003/0096290 | A1 | 5/2003 | Fruehauf et al. | 435/6 |
| 2004/0023375 | A1 | 2/2004 | Kornblith et al. | |
| 2004/0072722 | A1 | 4/2004 | Kornblith et al. | |
| 2004/0086888 | A1 | 5/2004 | Kornblith et al. | |
| 2007/0059821 | A1 | 3/2007 | Kornblith et al. | |
| 2008/0085519 | A1 | 4/2008 | Gabrin et al. | |

FOREIGN PATENT DOCUMENTS

| | | |
|---|---|---|
| WO | WO 96/10742 | 4/1996 |
| WO | WO 98/02038 | 1/1998 |
| WO | WO 98/02038 A1 | 1/1998 |
| WO | WO 01/65994 A2 | 9/2001 |
| WO | WO 01/79540 A2 | 10/2001 |
| WO | WO 02/33117 A2 | 4/2002 |
| WO | WO 2004/015065 A2 | 2/2004 |
| WO | WO 2004/035833 A1 | 4/2004 |

OTHER PUBLICATIONS

PL Kornblith et al., "Response variability of human brain tumors to AZQ in tissue culture," Journal of Neuro-Onocology, 1986, pp. 49-54, vol. 4, Martinus Nijhoff Publishers, Boston.

(Continued)

*Primary Examiner*—Ethan Whisenant
(74) *Attorney, Agent, or Firm*—Cooley LLP

(57) ABSTRACT

Methods are provided for accurately predicting efficacy of chemotherapeutic agents. Methods of the invention increase the positive predictive value of chemosensitivity assays by assessing both the ability of a chemotherapeutic to destroy cells and the genetic propensity of those cells for resistance. Results obtained using methods of the invention provide insight into the in vivo effectiveness of a therapeutic, and lead to more effective chemotherapeutic treatment.

29 Claims, No Drawings

OTHER PUBLICATIONS

RS Weinstein et al., "Ultrastructure of a cloned astrocytoma in tissue culture," Cancer, 1971, pp. 1174-1181, vol. 27.

PMcL Black et al., "Ultrastructural and electrophysiological features of meningioma whorls in tissue culture," Acta Neuropathol (Berl), 1979, vol. 46, pp. 33-38.

RM Scott et al., "Invasiveness in tissue culture: A technique for study of gliomas," Surg Forum, 1978, pp. 531-533, vol. 29.

T. Liszczak et al., "Morphological, biochemical, ultrastructural, tissue culture and clinical observations of typical and aggressive craniopharyngiomas," Acta Neuropathol (Berl), 1978, pp. 191-203, vol. 43.

PL Kornblith et al., "Growth-inhibitory effects of diphenylhydantoin on human brain tumor cells in culture," Neurosurgery, 1978, pp. 122-127, vol. 2.

RR Weichselbaum et al., "Characterization and radiobiologic parameters of medulloblastoma in vitro," Cancer, 1977, pp. 1087-1096, vol. 40.

RL Martuza et al., "Characteristics of human optic gliomas in tissue culture," J. Neurosurg, 1977, pp. 78-84, vol. 46.

MA Oberc-Greenwood, et al., "Ultrastructural features of the lymphocyte-stimulated halos produced by human glioma-derived cells in vitro," Journal of Neuro-Oncology, 1986, pp. 387-396, vol. 3.

BH Smith et al., "Membrane and cytoplasmic changes in 1,3-bis (2-chloroethy 1)- 1 -nitrosourea (BCNU)-sensitive and resistant human malignant glioma-derived cell lines," Journal of Neuro-Oncology, 1983, pp. 237-248, vol. 1.

GA Curt et al., "Phase II and pharmacokinetic study of aziridinyl-benzoquinone (2,5-diaziridinyl-3, 6-bis(carboethoxyamino)-1,4 benzoquinone, diaziquone, NSC 182986) in high grade gliomas," Cancer Research, 1983, pp. 6102-6105, vol. 43, Issue 12 pt 1.

N Shitara et al., "Flowcytometric and cytogenetic analysis of human cultured cell lines derived from high- and low-grade astrocytomas," Acta Neuropathol (Berl), 1983, pp. 40-48, vol. 60.

MK Gumerlock et al., "Chemical differentiation of cultured human glioma cells: Morphologic and immunologic effects," Surgical Forum, 1981, pp. 475-477, vol. XXXII.

PL Kornblith et al., "Growth-inhibitory effect of diphenylhydantoin on murine astrocytomas," Neurosurgery, 1979, pp. 259-263, vol. 5.

MC Trachtenberg et al., "Biophysical properties of cultured human glial cells," Brain Research, 1972, pp. 279-298, vol. 38.

J. Lightbody et al., "Biochemically differentiated clonal human glial cells in tissue culture," J. Neurobiology, 1970, pp. 411-417, vol. 1, No. 4.

PMcL Black et al., "Biophysical properties of human astrocytic brain tumor cells in cell nature," Journal of Cellular Physiology, 1980, pp. 565-570, vol. 105.

TM Liszczak et al., "Ultrastructure of human endometrial epithelium in monolayer culture with and without steroid hormones," In Vitro, 1977, pp. 344-356, vol. 13, No. 6.

TM Liszczak et al., "Procedure for the embedment and ultrastructural visualization of cells cultured on plastic microtest plates," Journal of Immunological Methods, 1977, pp. 131-134, vol. 15.

RM Stewart et al., "Glutamate accumulation by human gliomas and meningiomas in tissue culture," Brain Research, 1976, pp. 441-452, vol. 118.

PL Kornblith et al., "The future of therapy for glioblastoma," Surg Neurol, 1993, pp. 538-543, vol. 39.

PL Kornblith, "Management of malignant gliomas," Neurosurgery Quarterly, 1991, pp. 97-110, vol. 1, Issue 2.

PL Kornblith et al., "Chemotherapy for malignant gliomas," Journal of Neurosurgery, 1988, pp. 1-17, vol. 68, Issue 1.

PE McKeever et al., "Products of cells cultured from gliomas: VI. Immunofluorescent, morphometric, and ultrastructural characterization of two different cell types growing from explants of human gliomas," American Journal of Pathology, 1987, pp. 358-372, vol. 127, Issue 2.

PMcL Black et al., "Immunological, biological, ultrastructural, and electrophysiological characteristics of a human glioblastoma-derived cell culture line," J. Neurosurg., 1982, pp. 62-72, vol. 56.

PL Kornblith, "The role of cytotoxic chemotherapy in the treatment of malignant brain tumors," Surg Neurol, 1995, pp. 551-552, vol. 44.

WC Welch et al., "Morphologic immunologic, biochemical and cytogenetic characteristics of the human glioblastoma-derived cell line, SNB-19," Journal of the Society for In Vitro Biology, 1995, pp. 610-616, vol. 31.

E Sariban et al., "DNA crosslinking responses of human malignant glioma cell strains to chloroethylnitrosoureas, cisplatin and diaziquone," Cancer Research, 1987, pp. 3988-3994, vol. 47, Issue 15.

Abstract for JP 2003-199585, Database WPI Week 200377, Jul. 15, 2003, XP002450791.

Supplementary European Search Report based on International Application No. PCT/US2003/032285, (Oct. 8, 2007).

Alley, M., "Morphometric and Colorimetric Analyses of Human Tumor Cell Line Growth and Drug Sensitivity in Soft Agar Culture," Cancer Research, vol. 51, pp. 1247-1256 (1991).

Andreotti, P., "TCA-100 Tumour Chemosensitivity Assay: Differences in Sensitivity between: Cultured Tumour Cell Lines and Clinical Studies," J. Biolumin Chemilumin, vol. 9, pp. 373-378 (1994).

Arnold, J., et al., "Evaluation of Chemopreventive Agents in Different Mechanistic Classes Using a Rat Tracheal Epithelial Cell Culture Transformation Assay," Cancer Research, vol. 55, pp. 537-543 (1995).

Burczynski, M., et al., "Toxicogenomics-Based Discrimination of Toxic Mechanism in HepG2 Human Hepstoma Cells," Toxicological Sciences, vol. 58, No. 2, pp. 399-415 (2000).

Dietel, M., et al., "In Vitro Prediction of Cytostatic Drug Resistance in Primary Cell Cultures of Solid Malignant Tumours," Eur J Cancer, vol. 29A, No. 3, pp. 416-420 (1993).

Frykholm, G., et al., "Heterogeneity in Antigenic Expression and Radiosensitivity in Human Colon Carcinoma Cell Lines" In Vitro Cell Dev. Biol., vol. 27A, pp. 900-906 (1991).

Fulda, S., et al., "Antiproliferative Potential of Cytostatic Drugs on Neuroblastoma Cells In Vitro," Eur J of Cancer, vol. 31A, No. 4, pp. 616-621 (1995).

Gamboa, G., et al., "Characterization and Development of UCI 107, a Primary Human Ovarian Carcinoma Cell Line," Gynecologic Oncology, vol. 58, pp. 336-343 (1995).

Goldsworthy, T., et al., "Concepts, Labeling Procedures, and Design of Cell Proliferation Studies Relating to Carcinogenesis," Environmental Health Perspectives, vol. 101, supp. 5, pp. 59-66 (1993).

Gress, T., et al., "Development of a Database on Transcribed Sequences in Tumour Cells and Identification of Changes in Transcription Patterns Related to Transfomation and Other Tumour Cell Properties for the Global Finger Printing Analysis of Human Pancreatic Carcinoma cDNA Libraries," Biomed1. Health Res., vol. 24, pp. 171-181 (1998).

Hoffman, R., "The Three-Dimensional Question: Can Clinically Relevant Tumor Drug Resistance be Measured In Vitro?" Cancer and Metastasis Reviews, vol. 13, No. 2, pp. 169-173 (1994).

Kaaijk, P., et al., "Daunorubicin and Doxorubicin but not BCNU have Deleterious Effects on Organotypic Multicellular Spheroids of Gliomas," British Journal of Cancer, vol. 74, No. 2, pp. 187-193 (1996).

Kitamura, M., et al., "Chemosensitivity of Gastric Cancer Using Adhesive Tumor Cell Culture System," Oncology Reports, vol. 2, No. 1, pp. 27-31 (1995).

Kornblith, P., "Role of Tissue Culture in Prediction of Malignancy," Clinical Neurosurgery, vol. 25, pp. 346-376 (1978).

Kornblith, P., et al., "Variations in Response of Human Brain Tumors to BCNU In Vitro," Journal of Neurosurgery, vol. 48, No. 4, pp. 580-586 (1978).

Kruczynski, A., et al., "Evidence of a Direct Relationship Between the Increase in the In Vitro Passage Number of Human Non-Small-Cell-Lung Cancer Primocultures and their Chemosensitivity," Anticancer Research, vol. 13, pp. 507-514 (1993).

Persons, D., et al., "Interphase Molecular Cytogenetic Analysis of Epithelial Ovarian Carcinomas," American Journal of Pathology, vol. 142, No. 3, pp. 733-741 (1993).

International Search Report for PCT/US03/32285, dated Apr. 8, 2004 (4 pgs.).

Pfost et al., "A SNPshot: pharmacogenetics and the future of drug therapy," *TIBTECH* 18:334-338 (Aug. 2000).

Stephens, J.C., "Single-nucleotide Polymorphisms, Haplotypes, and Their Relevance to Pharmacogenetics," *Molecular Diagnosis* 4(4):309-317 (1999).

Broadley, et al., "A Tissue-Culture Model for the Study of Canine Vocal Fold Fibroblasts," *Laryngoscope* 105:23-27 (1995).

Cilley et al., "Fetal Lung Development: Airway Pressure Enhances the Expression of Developmental Genes," *Journal of Pediatric Surgery* 35(1):113-119 (Jan. 2000).

Dudley et al., "A human endometrial explant system: Validation and potential applications," *Am J Obstet Gynecol* 167(6):1774-1780 (Dec. 1992).

Freshney, R. I., *Culture of Animal Cells: A Manual of Basic Technique*, 2nd edition, pp. 107, 124-126, 179, 233-234, 290 (1987).

Gerweck et al., "Radiation Sensitivity of Cultured Human Glioblastoma Cells," *Radiology* 125(1):231-234 (1977).

Ghosh et al., "Immunohistological staining of reactive mesothelium, mesothelioma, and lung carcinoma with a panel of monoclonal antibodies," *J Clin Pathol* 40:19-25 (1987).

Guo et al., "Direct fluorescence analysis of genetic polymorphisms by hybridization with oligonucleotide arrays on glass supports," *Nucleic Acids Research* 22(24):5456-5465 (1994).

Kutamura et al., "Chemosensitivity of gastric cancer using adhesive tumor cell culture system," *Oncology Reports* 2:27-31 (1995).

Nance et al., "Immunocytochemical Panel for the Identification of Malignant Cells in Serous Effusions," *Am J Clin Pathol* 95(6):867-874 (Jun. 1991).

Pinkus et al., "Optimal Immunoreactivity of Keratin Proteins in Formalin-fixed Paraffin-embedded Tissue Requires Preliminary Trypsinization," *The Journal of Histochemistry and Cytochemistry* 33(5):465-473 (1985).

Raju, G.C., "The histological and immunohistochemical evidence of squamous metaplasia from the myoepithelial cells in the breast," *Histopathology* 17(3):272-275 (1990).

Singh et al., "Significance of Epithelial Membrane Antigen in the Work-Up of Problematic Serous Effusions," *Diagnostic Cytopathology* 13(1):3-7 (1995).

Stephens et al., "A longitudinal study of γ-interferon production by peripheral blood mononuclear cells from breast- and bottle-fed infants," *Clin Exp Immunol* 65:396-400 (1986).

Stewart et al., "Glutamate Accumulation By Human Gliomas and Meningiomas in Tissue Culture," *Brain Research* 118(3):441-452 (1976).

Stoop et al., "Identification of malignant cells in serious effusions using a panel of monoclonal antibodies Ber-EP4, MCA-b-12 and EMA," *Cytopathology* 3:297-302 (1992).

Tannock et al., *The Basic Science of Oncology*, 2nd edition, pp. 247-248, 261-265, 303-306(1992).

Wiseman, I.C., "A modification of Hepatest, using the Terasaki plate, for the Detection of $HB_SAg$ in blood donors," *J Clin Pathol* 29(3):264-266 (1976).

Becton-Dickinson Catalog, Anti-Cytokeratin (CAM 5.2) Reagent, pp. 1-11 (1997).

Boehringer Mannheim Catalog, Anti-Cytokeratin AE1/AE3, (1996).

DAKO Catalog, Specification Sheet for Monoclonal Mouse Anti-Human Epithelial Membrane Antigen, pp. 1-2 (1996).

\* cited by examiner

METHODS FOR ASSESSING EFFICACY OF CHEMOTHERAPEUTIC AGENTS

RELATED APPLICATIONS

This application is a continuation of U.S. application Ser. No. 11/713,662, filed Mar. 5, 2007 now U.S. Pat. No. 7,575,868, which is a continuation of U.S. application Ser. No. 10/336,659 filed Jan. 2, 2003, now abandoned which claims priority to U.S. Application No. 60/417,439, filed Oct. 12, 2002. The entire disclosures of the prior applications are incorporated by reference herein.

FIELD OF THE INVENTION

The invention relates to methods for assessing efficacy of chemotherapeutic agents.

BACKGROUND

Cancer chemotherapy involves the use of cytotoxic drugs to destroy unwanted cells in patients. Treatment may consist of using one or more cytotoxic drugs, depending on the nature of the disease being treated. However, drug toxicity and drug resistance are significant barriers effective chemotherapy.

Toxicity from chemotherapeutic agents produces side effects ranging from mild trauma to death. Moreover, repeated exposure to chemotherapeutic drugs is itself often fatal. As chemotherapeutic drugs are carried in the blood, they are taken up by proliferating cells, including normal cells. Tissues with high growth rates such as bone marrow and epithelial tissues, including the gastrointestinal tract, are normally most susceptible to toxic side effects. Some drugs have additional toxic effects on other tissues, such as the urinary tract, myocardium, or pancreas. Chemotherapeutic agents may cause direct injury to the heart, either acutely, in the form of myocardial tissue injury or dysrhythmias, or in a delayed or chronic fashion associated with congestive heart failure.

Target cells, such as malignant or diseased cells, may be intrinsically resistant to chemotherapeutic drugs or they may acquire resistance as a result of exposure. A target cell may be genetically predisposed to resistance to particular chemotherapeutics. Alternatively, the cell may not have receptors or activating enzymes for the drug or may not be reliant on the biochemical process with which the drug interferes. Additionally, individuals may be inherently resistant to a drug due to altered disposition of the drug in organs other than the tumor. These mechanisms include, but are not limited to, rapid metabolism to inactive species, failure to metabolize to an active species of drug, and rapid clearance or sequestration. Many of these aspects are encoded genetically by normal polymorphisms in metabolic genes that act primarily, but not exclusively, in the liver and gastrointestinal tract and the kidneys.

Acquired resistance also may develop after cells have been exposed to a drug or to similar classes of drugs. One example of acquired drug resistance is the multiple drug resistance phenotype. Multiple drug resistance is a phenomenon of cross-resistance of cells to a variety of chemotherapeutic agents which are not structurally or functionally related. This phenomenon is typically mediated by p-glycoprotein, a cell membrane pump that is present normally on the surface of some epithelial cells. The protein actively removes drug from the cell, making it resistant to drugs that are substrates for the cell membrane pump.

A critical issue in cancer chemotherapy is the ability to select drugs that not only affect cancer cell phenotype in cell culture assays, but are also not subject to resistance whether in the tumor or intrinsic to the patient. The present invention addresses that issue.

SUMMARY OF THE INVENTION

The invention provides methods for accurately predicting efficacy of chemotherapeutic agents. Methods of the invention increase the positive predictive value of chemosensitivity assays by assessing both the ability of a chemotherapeutic to affect tumor cells phenotype and the genetic propensity of the patient for resistance to the chemotherapeutic. Results obtained using methods of the invention provide insight into the in vivo effectiveness of a therapeutic, and lead to more effective, individualized, chemotherapeutic choices.

According to the invention, a phenotype assay screens a therapeutic candidate for the ability to affect the phenotype of tumor cells in culture. A therapeutic candidate that produces the desired phenotypic effect (e.g., cell death, decreased motility, changes in cellular adhesion, angiogenesis, or gene expression, among others) then is screened against genetic properties of cells of the patient which make resistance to the therapeutic candidate likely or possible. A therapeutic candidate that has a desired phenotypic effect on patient tumor cells and that does not appear to be subject to genetic-based resistance is selected for use. As a result of combining phenotypic and genetic data, use of the invention increases the likelihood that a therapeutic candidate, chosen on the basis of its ability to affect cellular phenotype, will be effective when administered to patients.

Accordingly, the invention provides methods for assessing efficacy of chemotherapeutic agents comprising exposing cells to a chemotherapeutic agent, conducting an assay to determine whether the chemotherapeutic agent affects tumor cell phenotype, and identifying genetic characteristics of cells of the patient (which may or may not be tumor cells) that indicate a propensity for resistance to the chemotherapeutic agent.

In a preferred embodiment, a phenotypic assay for use in the invention comprises obtaining a tumor explant from a patient, culturing portions of the explant, growing a monolayer of relevant cells from the explant, exposing the monolayer to a drug candidate, and assessing the ability of the drug candidate to alter tumor cell phenotype. A preferred phenotypic assay is disclosed in U.S. Pat. No. 5,728,541, and in co-owned, co-pending U.S. application Ser. No. 10/208,480, both of which are incorporated by reference herein.

Genotype analysis according to the invention is accomplished by any known method. A preferred method comprises comparing the genotype, or portion thereof, of cells obtained from the patient with genotypes known to be associated with drug resistance generally, or specifically with respect to a therapeutic candidate being evaluated. For example, the existence in patient cells of a polymorphic variant that is known or suspected to confer resistance to a therapeutic candidate would screen that candidate out as a potential therapeutic against those cells. Genetic characteristics of patient cells are determined by methods known in the art (e.g., sequencing, polymorphisms) as set forth below. The impact of a patient's genotype upon drug resistance may be determined by reference to genetic databases or libraries that catalog known mutations or polymorphisms related to resistance.

The present invention also provides methods for selecting a chemotherapeutic agent for treating a patient based on results obtained from the phenotypic and genotypic assays. In a preferred embodiment, the present invention allows for the assessment of whether a chemotherapeutic agent will be effective in treating a cancer when administered to a patient. According to the invention, chemotherapeutic agents or combinations of chemotherapeutic agents are selected for treatment where an effect on cellular phenotype is observed and characteristics of genetic-based resistance are not observed.

Methods of the invention are useful in drug or chemotherapeutic agent screening to provide information indicative of the in vivo reactivity of the cells, and thus the specific efficacy as to a particular patient. Methods of the invention are also useful to screen new drug candidates for therapeutic efficacy and to provide a basis for categorizing drugs with respect to the tumor types against which they will work best.

A phenotypic assay according to the invention is conducted on cells obtained from a tumor explant from a patient. Genotypic assays of the invention are performed on genetic data obtained from patient cells, regardless of their source. Thus, a genotypic assay can be performed on somatic cells obtained from the patient or on cells from the same tumor that is evaluated in the phenotypic assay. Assays of the invention can be performed on an individualized basis or on a pool of samples obtained from multiple individual patients. If assays are conducted on pooled samples, the phenotypic characteristics of the pool of samples are determined followed by individualized genotypic assays on specific patients. This allows multiplexing of the phenotypic portion of the assay.

DETAILED DESCRIPTION OF THE INVENTION

This invention provides methods for assessing efficacy of chemotherapeutic agents. Specifically, the invention provides methods for assessing the efficacy of chemotherapeutic agents based on phenotypic changes observed in tumor cells obtained from a patient and genetic characteristics of the patient that indicate general or specific chemotherapeutic resistance. In one aspect of the invention, efficacy of a chemotherapeutic agent is assessed based upon the results of the phenotypic and genotypic assays. In another aspect of the invention, chemotherapeutic agents are selected for treating a patient based on the results of the phenotypic and genotypic assays.

The present invention is also useful for screening of therapeutic agents against other diseases, including but not limited to, hyperproliferative diseases, such as psoriasis. In addition, the screening of agents that retard cell growth (anti-cancer, anti-proliferative), including agents that enhance or subdue intracellular biochemical functions, are evaluated using methods of the present invention. For example, the effects of therapeutics on the enzymatic processes, neurotransmitters, and biochemical pathways are screened using methods of the invention. Methods of the invention can be practiced on any type of cell obtained from a patient, including, but not limited to, normal somatic cells, malignant cells, abnormal proliferating cells, and other diseased cells. Cells are obtained from any patient sample, including, but not limited to, tumors, blood samples and buccal smears. The skilled artisan recognizes that methods of the invention can be practiced using a variety of different samples.

In one step of the invention, a phenotype assay is employed to assess sensitivity and resistance to chemotherapeutic agents. The phenotypic assay is performed in vitro using cultured cells. The phenotype assay allows for identification and separation of target cells from other cells found in a tissue sample, as well as direct measurement and monitoring of target cells in response to chemotherapeutic treatment. Direct measurements and monitoring of live cells are performed using known methods in the art including, for example, the measuring of doubling rate, fraction proliferative assays, monitoring of cytostasis, cell death, cell adhesion, gene expression, angiogenesis, cell motility, and others. Direct measurements also include known assays, such as those directed to measurement and monitoring of apoptosis, senescence, and necrosis.

In another step of the invention, a genotype assay is performed to determine whether cells from a patient comprise a genetic characteristic associated with resistance to the chemotherapeutic agents. Genotype assays reveal latent resistance to chemotherapeutic agents not observed by phenotypic assays. Genotypic assays may measure characteristics, such as metabolism, toxic effects, absorption of a therapeutic candidate.

In one embodiment of the invention, the phenotypic assay is performed using cell culture monolayers prepared from tumor cells. In a preferred embodiment, monolayers are cultured from cohesive multicellular particulates generated from a tumor biopsy. Explants of tumor tissue sample are prepared non-enzymatically, for initial tissue culture monolayer preparation. The multicellular tissue explant is removed from the culture growth medium at a predetermined time to both allow for the growth of target cells and prevent substantial growth of non-target cells such as fibroblasts or stromal cells.

By way of example, in one embodiment of the invention, a cell culture monolayer is prepared in accordance with the invention using the following procedure. A biopsy of non-necrotic, non-contaminated tissue is obtained from a patient by any suitable biopsy or surgical procedure known in the art. In a preferred embodiment, the tissue sample is tumor tissue. The size of the biopsy sample is not central to the methods provided herein, but a sample is preferably about 5 to 500 mg, and more preferably about 100 mg. Biopsy sample preparation generally proceeds under sterile conditions. Cohesive multicellular particulates (explants) are prepared from the tissue sample by enzymatic digestion or mechanical fragmentation. Ideally, mechanical fragmentation of the explant occurs in a medium substantially free of enzymes that are capable of digesting the explant. For example, the tissue sample may be minced with sterile scissors to prepare the explants. In a particularly preferred embodiment, the tissue sample is systematically minced by using two sterile scalpels in a scissor-like motion, or mechanically equivalent manual or automated opposing incisor blades. This cross-cutting motion creates smooth cut edges on the resulting tissue multicellular particulates. After the tissue sample has been minced, the particles are plated in culture flasks (for example, 9 explants per T-25 flask or 20 particulates per T-75 flask). The explants are preferably evenly distributed across the bottom surface of the flask, followed by initial inversion for about 10-15 minutes. The flask is then placed in a non-inverted position in a 37° C. $CO_2$ incubator for about 5-10 minutes. In another embodiment in which the tissue sample comprises brain cells, the flasks are placed in a 35° C., non-$CO_2$ incubator. Flasks are checked regularly for growth and contamination.

The multicellular explant is removed from the cell culture at a predetermined time, as described below. Over a period of a few weeks a monolayer is produced. With respect to the culturing of tumor cells, it is believed (without any intention of being bound by the theory) that tumor cells grow out from the multicellular explant prior to contaminating stromal cells. Therefore, by initially maintaining the tissue cells within the explant and removing the explant at a predetermined time, growth of the tumor cells (as opposed to stromal cells) into a monolayer is facilitated. The use of the above procedure to form a cell culture monolayer maximizes the growth of tumor cells from the tissue sample, and thus optimizes the phenotypic and genotypic assays.

Once a primary culture and its derived secondary monolayer tissue culture has been initiated, the growth of the cells is monitored to oversee growth of the monolayer and ascertain the time to initiate the phenotypic assay. Prior to the phenotypic assay, monitoring of the growth of cells may be conducted by visual monitoring of the flasks on a periodic basis, without killing or staining the cells and without removing any cells from the culture flask. Data from periodic counting or measuring is then used to determine growth rates or cell motility, respectively.

Phenotypic assays are performed on cultured cells using a chemotherapeutic drug response assay with clinically relevant dose concentrations and exposure times. One embodiment of the present invention contemplates a phenotypic assay that assesses whether chemotherapeutic agents effect cell growth. Monolayer growth rate is monitored using, for example, a phase-contrast inverted microscope. In one embodiment, culture flasks are incubated in a (5% $CO_2$) incubator at about 37° C. The flask is placed under the phase-contrast inverted microscope, and ten fields (areas on a grid inherent to the flask) are examined using a 10× objective. In general, the ten fields should be non-contiguous, or significantly removed from one another, so that the ten fields are a representative sampling of the whole flask. Percentage cell occupancy for each field examined is noted, and averaging of these percentages then provides an estimate of overall percent confluency in the cell culture. When patient samples have been divided between two more flasks, an average cell count for the total patient sample should be calculated. The calculated average percent confluency should be entered into a process log to enable compilation of data—and plotting of growth curves—over time. Alternatively, confluency is judged independently for each flask. Monolayer cultures may be photographed to document cell morphology and culture growth patterns. The applicable formula is:

$$\text{Percent confluency} = \frac{\text{estimate of the area occupied by cells}}{\text{total area in an observed field}}$$

As an example, therefore, if the estimate of area occupied by the cells is 30% and the total area of the field is 100%, percent confluency is 30/100, or 30%.

Following initial culturing of the multicellular tissue explant, the tissue explant is removed from the growth medium at a predetermined time. In one embodiment, the explant is removed from the growth medium prior to the emergence of a substantial number of stromal cells from the explant. Alternatively, the explant may be removed according to the percent confluency of the cell culture. In one embodiment of the invention, the explant is removed at about 10 to about 50 percent confluency. In a preferred embodiment of the invention, the explant is removed at about 15 to about 25 percent confluency. In a particularly preferred embodiment, the explant is removed at about 20 percent confluency. By removing the explant in either of the above manners, a cell culture monolayer predominantly composed of target cells (e.g., tumor cells) is produced. In turn, a substantial number of non-target cells, such as fibroblasts or other stromal cells, fail to grow within the culture. Ultimately, this method of culturing a multicellular tissue explant and subsequently removing the explant at a predetermined time allows for increased efficiency in both the preparation of cell cultures and subsequent phenotypic and genotypic assays for assessing efficacy of chemotherapeutic agents.

In another embodiment, a phenotypic assay assesses whether chemotherapeutic agents effect cell motility. Methods for measuring cell motility are known by persons skilled in the art. Generally, these methods monitor and record the changes in cell position over time. Examples of such methods include, but are not limited to, video microscopy, optical motility scanning (for example, see U.S. Pat. No. 6,238,874, the disclosure of which is incorporated by reference herein) and impedance assays. In a preferred embodiment, cell motility assays are carried out using monolayer cultures of malignant cells as described herein.

Cell culture methods of the invention permit the expansion of a population of proliferating cells in a mixed population of abnormal proliferating cells and other (normal) cells. The mixed population of cells typically is a biopsy or sample from a solid tumor. A tissue sample from the patient is harvested, cultured and analyzed for genetic indicia of resistance to chemotherapeutics. Subcultures of the cells produced by the culture methods described above may be separately exposed to a plurality of treatments and/or therapeutic agents for the purpose of objectively identifying the best treatment for the patient. By way of example, procedures for culturing the malignant cells and determining a phenotypic to a chemotherapeutic agent may be performed in the following manner. First, a specimen is finely minced and tumor fragments are plated into tissue culture. The cells are then exposed to growth medium, such as a tumor-type defined media with serum. The cells are trypsinized, preferably, but not necessarily, when greater than 150,000 cells grown out from tumor fragment. The cells are preferably plated into a Terasaki plate at 350 cells per well. The cells are analyzed to verify that a majority of cells are tumor epithelial cells. Non-adherent cells are removed from the wells. The cells are treated with 6 concentrations and 2 control lanes of chemotherapeutic agent or agents for preferably 2 to 4 hours. The chemotherapeutic agents are removed by washing. The cells are incubated for preferably 3 days. The living cells are counted to calculate the kill dose that reduces by 40% the number of cells per well from control wells.

The culture techniques of the present invention result in a monolayer of cells that express cellular markers, secreted factors and tumor antigens in a manner representative of their expression in vivo. Specific method innovations such as tissue sample preparation techniques render this method practically, as well as theoretically, useful.

According to the present invention, cells from a patient are analyzed for genetic characteristics (abnormalities) specific to a patient. Genetic characteristic of a cell or cell population can be analyzed alone or in combination with other characteristics. Genetic characteristics of the invention can be, without limitation, a genetic polymorphism or a mutation, such as an insertion, inversion, deletion, or substitution. In one embodiment, nucleic acids are isolated from cells of a patient and analyzed to identify genotypic characteristics of the cells. The isolated nucleic acid is DNA or RNA. The nucleic acid, preferably, is analyzed in a microarray for DNA-encoded polymorphisms in the coding or control regions of the gene. In another embodiment, the nucleic acid is analyzed in a microarray for aberrant expression of one or more genes. In this embodiment, the microarray contains nucleic acids that are characteristic of known malignancies, as well as nucleic acids, that are not correlated with known malignancies so that previously unknown relationships between gene expression and a proliferative disease or condition may be identified.

A preferred method of the invention comprises comparing the genotype, or portion thereof, of cells from a patient with genotypes known to be associated with drug resistance generally, or specifically with respect to a therapeutic candidate being evaluated. For example, the existence in patient cells of a polymorphic variant that is known or suspected to confer resistance to a therapeutic candidate would screen that candidate out as a potential therapeutic against those cells.

Methods for isolating and analyzing nucleic acids derived from the cells are known in the art. The presence of known proliferation markers, such as the aberrant expression of one or more genes, the epidermal growth factor receptor (EGFR) cyclin D1, p16cyclin-kinase inhibitor, retinoblastoma (Rb), transforming Growth-Factor β (TGFβ) receptor/smad, MDM2 or p53 genes, may be determined by, for example, northern blotting or quantitative polymerase chain reaction (PCR) methods (i.e., RT-PCR).

In one embodiment of the present invention, mRNA (polyA$^+$ mRNA) is isolated and labeled cDNA is prepared therefrom. The labeled cDNA is prepared by synthesizing a first strand cDNA using an oligo-dT primer, reverse transcriptase and labeled deoxynucleotides, such as, Cy5-dUTP, commercially available from Amersham Pharmacia Biotech. Radio-labeled nucleotides also can be used to prepare cDNA probes. The labeled cDNA is hybridized to the microarray under sufficiently stringent conditions to ensure specificity of hybridization of the labeled cDNA to the array DNA.

In another embodiment of the invention, the labeled array is visualized. Visualization of the array may be conducted in a variety of ways. For instance, when the reading of the microarray is automated and the labeled DNA is labeled with a fluorescent nucleotide, the intensity of fluorescence for each discreet DNA of the microarray can be measured automatically by a robotic device that includes a light source capable of inducing fluorescence of the labeled cDNA and a spectrophotometer for reading the intensity of the fluorescence for each discreet location in the microarray. The intensity of the fluorescence for each DNA sample in the microarray typically is directly proportional to the quantity of the corresponding species of mRNA in the cells from which the mRNA is isolated. It is possible to label cDNA from two cell types (i.e., normal and diseased proliferating cells) and hybridize equivalent amounts of both probe populations to a single microarray to identify differences in RNA expression for both normal and diseased proliferating cells. Tools for automating preparation and analysis of microarray assays, such as robotic microarrayers and readers, are available commercially from companies such as Gene Logic and Nanogen and are under development by the NHGRI. The automation of the microarray analytical process is desirable and, for all practical purposes necessary, due to the huge number and small size of discreet sites on the microarray that must be analyzed.

In a further embodiment, DNA microarrays are used in combination with the cell culturing method of the present invention due to the increased sensitivity of mRNA quantification protocols when a substantially pure population of cells are used. For their ease of use and their ability to generate large amounts of data, microarrays are preferred, when practicable. However, certain other or additional qualitative assays may be preferred in order to identify certain markers.

In another embodiment, the presence of, or absence of, specific RNA or DNA species are identified by PCR procedures. Known genetic polymorphisms, translocations, or insertions (i.e., retroviral insertions or the insertion of mobile elements, such as transposons) often can be identified by conducting PCR reactions with DNA isolated from cells cultured by the methods of the present invention. Where the sequence anomalies are located in exons, the genetic polymorphisms may be identified by conducting a PCR reaction using a cDNA template. Aberrant splicing of RNA precursors also may be identified by conducting a PCR reaction using a cDNA template. An expressed translocated sequence may be identified in a microarray assay, such as the Affymetrix p53 assay.

In one embodiment, small or single nucleotide substitutions are identified by the direct sequencing of a given gene by the use of gene-specific oligonucleotides as sequencing primers. In a further embodiment, single nucleotide mutations are identified through the use of allelic discrimination molecular beacon probes, such as those described in Tyagi, S. and Kromer, F. R. (1996) *Nature Biotech.* 14:303-308 and in Tyagi, S. et al., (1998) *Nature Biotech.* 16:49-53, the disclosures of each of which are incorporated by reference herein.

Genotypic analysis may be based on experimentation or experience. Sources for such empirical data made be obtained from, but not limited to clinical records and/or animal tumor transplant studies. Genetic characteristics found in the patient cells can be compared to a database containing known tumor genotypes and their respective resistance to chemotherapeutic agents. In a preferred embodiment, a database containing genotypes and their respective drug resistance profile is used to compare genotypic characteristics of the target cells to resistance to chemotherapeutic agents in vivo. Computer algorithms are useful for carrying out pattern matching routines in complex systems, such as genetic data-mining. A linear regression algorithm, for example, can be utilized to analyze a database and identify the genotype most closely matching the genetic characteristics in the patient cells. In one embodiment, a comparative analysis of genotypes is performed using a known linear regression algorithm.

According to the invention, genotypic characteristics of patient cells are analyzed to establish whether such characteristics are associated with resistance to chemotherapeutic agents in vivo. While the above-mentioned genotypic assays are useful in the analysis of nucleic acids derived from cells produced by the culture methods embodied in the present invention, numerous additional methods are known in the general fields of molecular biology and molecular diagnostics that may be used in place of the above-referenced methods. Information obtained from genotypic assays is analyzed to determine efficacy of chemotherapeutic agents.

In a further embodiment of the invention, data obtained by practicing the methods of the invention, including phenotypic, genotypic and patient outcome information, is stored in databases. The contents of these databases include, but are not limited to, observed in vitro phenotypes (disease factors) and genotypes (host factors). By applying analytical techniques to the stored information, predictions of chemotherapeutic efficacy can be made. Methods of the invention allow for the skilled practitioner to accurately select an effective course of chemotherapy for a patients, thus reducing the risk of treatment-related trauma and resistance.

In one aspect of the invention, a course of chemotherapy is selected based on results obtained from the phenotypic and genotypic assays. The present invention allows for the assessment of the likelihood of whether chemotherapeutic agents will be effective in treating a malignancy in a patient. A phenotypic assay in combination with a genotypic assay operates to minimize the risk of administering to a patient a chemotherapeutic agent or combinations of chemotherapeutic agents to which the tumor is resistant. In one aspect of the invention, chemotherapeutic agents or combinations of chemotherapeutic agents are selected for treatment where an effect on cellular phenotype is observed and the genotypic characteristics associated with resistance are not observed.

Chemotherapeutic agents that effect cellular phenotype are potential candidates for use in the patient. Known procedures that screen for chemotherapeutic agents are time-consuming and expensive. In one embodiment of the invention, chemotherapeutic agents that effect cellular phenotype and lack genetic changes associated with drug resistance are administered to the patient. In a further embodiment, genotypic characteristics observed in the genetic assay undergo a comparative analysis to determine if such characteristics are associated with drug resistance. In another embodiment, the phenotypic and genotypic assays are performed in succession, thereby narrowing the scope of the genotypic comparative analysis, and reducing labor costs and associated expenses. In one aspect of the invention, when it is determined that a chemotherapeutic agent effects cellular phenotype and is not associated with resistance to cells having the genotypic change, a patient is treated with the chemotherapeutic agent.

The following examples provide further details of methods according to the invention. For purposes of exemplification, the following examples provide details of the use of methods of the present invention in cancer treatment. Accordingly, while exemplified in the following manner, the invention is not so limited and the skilled artisan will appreciate its wide range of application upon consideration thereof.

Example 1

A patient was diagnosed with breast cancer and chemotherapeutic treatment was prescribed by the treating physician. A tumor biopsy of approximately 100 mg of non-necrotic, non-contaminated tissue was harvested from the patient by surgical biopsy and transferred to a laboratory in a standard shipping container. Biopsy sample preparation proceeded as follows. Reagent grade ethanol was used to wipe down the surface of a Laminar flow hood. The tumor was then removed, under sterile conditions, from its shipping container, and cut into quarters with a sterile scalpel. Using sterile forceps, each undivided tissue quarter was then placed in 3 ml sterile growth medium (Standard F-10 medium containing 17% calf serum and a standard amount of Penicillin and Streptomycin) and minced by using two sterile scalpels in a scissor-like motion. After each tumor quarter was minced, the particles were plated in culture flasks using sterile pasteur pipettes (9 explants per T-25 or 20 particulates per T-75 flask). Each flask was then labeled with the patient's code and the date of explantation. The explants were evenly distributed across the bottom surface of the flask, with initial inverted incubation in a 37° C. incubator for 5-10 minutes, followed by addition of about 5-10 ml sterile growth medium and further incubation in the normal, non-inverted position. Flasks were placed in a 35° C., non-$CO_2$ incubator. Flasks were checked daily for growth and contamination as the explants grew out into a cell monolayer.

Following initiation of prime cell culture of the tumor specimen, cells were removed from the monolayers grown in the flasks for centrifugation into standard size cell pellets. Each cell pellet was then suspended in 5 ml of the above-described medium and was mixed in a conical tube with a vortex for 6 to 10 seconds, followed by manual rocking back and forth 10 times. A 36 ml droplet from the center of each tube was then pipetted into one well of a 96-well microtiter plate together with an equal amount of trypan blue, plus stirring. The resulting admixture was then divided between two hemocytometer quadrants for examination using a standard light microscope. Cells were counted in two out of four hemocytometer quadrants, under 10× magnification—only those cells which did not take up the trypan blue dye were counted. This process was repeated for the second counting chamber. An average cell count per chamber was calculated, and the optimum concentration of cells in the medium was determined.

Accommodating the above calculations, additional cell aliquots from the 4 monolayers were separately suspended in growth medium via vortex and rocking and were loaded into a Terasaki dispenser adapted to a 60-well plate. Aliquots of the prepared cell suspension were delivered into the microtiter plates using Terasaki dispenser techniques. Cells were plated into 60-well microtiter plates at a concentration of 100 cells per well.

Twenty-four hours post-plating, the chemotherapeutic agent paclitaxel sold under the trademark TAXOL (Bristol-Myers Squibb Company) was applied to the wells in the microtiter plates. Three treatment rows in the plates (Rows 2, 3, and 4) were designed to have escalating paclitaxel doses (1.0, 5.0, and 25 µM). Row 5 served as a control. The paclitaxel exposure time was two hours. The cells were allowed to incubate for another 72 hours so that inhibition of cell proliferation can be observed. During this period, the growth inhibiting effect of paclitaxel was monitored by observing the percent of confluency of the cells. For each microtiter well, the percent of confluency of cultured cells was plotted as a function of time.

Since paclitaxel affected growth rate of the cultured cells, cells from the patient were subjected to genotypic analysis. DNA was isolated from cells of the patient and analyzed for single nucleotide genetic polymorphisms. Known genetic polymorphisms were identified in the DNA by conducting PCR reactions and sequencing or SNP detection by hybridizations of a region of interest in the DNA. The DNA region of interest from the patient cells was compared to corresponding regions from known genetic banks and libraries (for example, GENBANK).

The phenotypic and genotypic assays were used in combination to determine that paclitaxel was an efficacious course of treatment for the patient. As a result, paclitaxel was administered to the patient.

Example 2

A patient was diagnosed with lung cancer and chemotherapeutic treatment was prescribed by the treating physician. A tumor biopsy of approximately 100 mg of non-necrotic, non-contaminated tissue was harvested from the patient by surgical biopsy and transferred to a laboratory in a standard shipping container. The biopsy sample was prepared as described in Example 1. Twenty-four hours post-plating, the chemotherapeutic agent carboplatin sold under the trademark PARAPLATIN (Bristol-Myers Squibb Company) was applied to the wells in the microtiter plates. The first three treatment rows in the plates (Rows 2, 3, and 4) were designed to have escalating carboplatin doses (50, 200, and 1000 µM). Row 5 serves as a control. The carboplatin exposure time was two hours. The cells were allowed to incubate for another 72 hours so that inhibition of cell motility can be observed.

Cell motility was measured by calculating the distance a cell travels over time. Cells were monitored using a digital video-camera mounted on a phase-contrast light microscope. To maintain the growth medium at 35° C., the microscope was fitted with a heated slide stage. After the cultured cells were incubated with carboplatin, cell migration was recorded under appropriate magnification (usually between 40× and 200x). During this period, the motility inhibiting effect of carboplatin was documented by plotting the distance cells travel as a function of time. The distance cells travel was a determined using digital imaging techniques known in the art.

Since carboplatin affected cell motility in the tumor cells, the cells were subjected to genotypic analysis by comparing DNA from the cultured cells to known genetic banks and libraries. Known genetic polymorphisms were identified in the cultured cells by conducting PCR reactions and sequencing a region of interest in DNA isolated from the cultured cells. The DNA region of interest from the cultured cells was compared to corresponding regions from known genetic banks and libraries (for example, GENBANK).

Genetic characteristics observed in the genotypic assay were compared to a database of genetic characteristics that were known to be associated with resistance to carboplatin. The phenotypic and genotypic assays were used in combination to determine that carboplatin was an efficacious course of treatment for the patient. As a result, carboplatin was administered to the patient.

While the invention has been shown and described with reference to specific preferred embodiments, it should be understood by those skilled in the art that various changes in form and detail may be made therein without departing from the spirit and scope of the invention as defined by the following claims.

What is claimed is:

1. A method of determining a responsive patient population for a chemotherapeutic drug candidate comprising:
   preparing multicellular tumor tissue explants from patient specimens;
   allowing the multicellular tumor tissue explants to form cell culture monolayers, and
      removing the explants from the culture when the monolayer is at about 10 to about 50 percent confluency and growing the monolayer, thereby preventing substantial growth of stromal cells;
   optionally preparing a subculture from the monolayer cells;
   conducting at least one phenotypic assay on cells from the monolayers or the subcultures,
      the phenotypic assay being predictive of the drug's efficacy; and
   optionally, conducting at least one genotypic analysis of cells from the patients to determine the presence or absence of a genotype predictive of resistance to said drug;
   thereby determining a responsive patient population for the chemotherapeutic drug candidate.

2. The method of claim 1, wherein said tumor tissue explants comprise malignant cells.

3. The method of claim 1, wherein the explants are from a solid tumor.

4. The method of claim 1, wherein the explants are prepared by mechanical fragmentation of tumor tissue in a medium substantially free of enzymes that are capable of digesting the explants.

5. The method of claim 1, wherein the explants are prepared by systematic mincing of the tumor tissue.

6. The method of claim 1, wherein the multicellular tissue explants are removed from the culture when the monolayers are at from about 15% to about 30% confluency.

7. The method of claim 1, wherein the at least one phenotypic assay comprises a drug response assay.

8. The method of claim 7, wherein the drug response assay measures one or more of cell death, cell growth, apoptosis, changes in cell motility, changes in cell adhesion, or changes in gene expression upon exposure of the cultured cells to a drug.

9. The method of claim 1, wherein the at least one phenotypic assay comprises an assay for expression of a cellular marker, secreted factor, or tumor antigen.

10. The method of claim 1, wherein the at least one phenotypic assay comprises an assay for aberrant gene expression.

11. The method of claim 1, wherein the genotype is an allelic variant and/or a single nucleotide polymorphism.

12. The method of claim 1, wherein the genotypic analysis is conducted on somatic cells from the patient.

13. The method of claim 1, wherein the genotypic analysis is conducted on a blood sample or a buccal smear from the patient.

14. The method of claim 1, wherein the genotypic analysis is conducted on cells of the monolayer or the subculture.

15. The method of claim 1, wherein the patient specimens are different tumor types.

16. The method of claim 1, wherein the genotypic analysis is predictive of one or more of drug metabolism, drug toxicity, and drug absorption.

17. A method for categorizing a chemotherapeutic drug candidate comprising:
   preparing multicellular tumor tissue explants from patient specimens;
   allowing the multicellular tumor tissue explants to form cell culture monolayers, and
      removing the explants from the culture when the monolayer is at about 10 to about 50 percent confluency and growing the monolayer, thereby preventing substantial growth of stromal cells;
   optionally preparing a subculture from the monolayer cells;
   conducting at least one phenotypic assay on cells from the monolayers or the subcultures,
      the phenotypic assay being predictive of the drug's efficacy; and
   optionally, conducting at least one genotypic analysis of cells from the patients to determine the presence or absence of a genotype predictive of resistance to said drug;
   thereby categorizing the chemotherapeutic drug candidate.

18. The method of claim 17, wherein the patient specimens are different tumor types.

19. The method of claim 17, wherein said tumor tissue explants comprise malignant cells.

20. The method of claim 17, wherein the explants are from a solid tumor.

21. The method of claim 17, wherein the explants are prepared by mechanical fragmentation of tumor tissue in a medium substantially free of enzymes that are capable of digesting the explants.

22. The method of claim 17, wherein the explants are prepared by systematic mincing of the tumor tissue.

23. The method of claim 17, wherein the multicellular tissue explants are removed from the culture when the monolayers are at from about 15% to about 30% confluency.

24. The method of claim 17, wherein the at least one phenotypic assay comprises a drug response assay.

25. The method of claim 24, wherein the drug response assay measures one or more of cell death, cell growth, apoptosis, changes in cell motility, changes in cell adhesion, or changes in gene expression upon exposure of the cultured cells to a drug.

26. The method of claim 17, wherein the at least one phenotypic assay comprises an assay for expression of a cellular marker, secreted factor, or tumor antigen.

27. The method of claim 17, wherein the at least one phenotypic assay comprises an assay for aberrant gene expression.

28. The method of claim 17, wherein the genotype is an allelic variant and/or a single nucleotide polymorphism.

29. The method of claim 17, wherein the genotypic analysis is predictive of one or more of drug metabolism, drug toxicity, and drug absorption.

* * * * *